United States Patent
Nair et al.

(10) Patent No.: US 7,105,580 B2
(45) Date of Patent: Sep. 12, 2006

(54) POROUS STRUCTURES USEFUL FOR GROWING LIVING TISSUE, AND METHODS OF MANUFACTURE

(75) Inventors: Prabha D. Nair, Trivandrum (IN); Buddy D. Ratner, Seattle, WA (US); Viola Vogel, Seattle, WA (US); Robert M. Nerem, Atlanta, GA (US)

(73) Assignee: University of Washington, Seattle, WA (US)

(*) Notice: Subject to any disclaimer, the term of this patent is extended or adjusted under 35 U.S.C. 154(b) by 438 days.

(21) Appl. No.: 10/314,453

(22) Filed: Dec. 5, 2002

(65) Prior Publication Data

US 2003/0215946 A1    Nov. 20, 2003

Related U.S. Application Data

(60) Provisional application No. 60/339,129, filed on Dec. 6, 2001.

(51) Int. Cl.
*B01J 13/00* (2006.01)
*C12N 5/00* (2006.01)
*C12N 5/02* (2006.01)

(52) U.S. Cl. .................. 516/98; 516/103; 516/109; 435/395

(58) Field of Classification Search ............ None
See application file for complete search history.

(56) References Cited

U.S. PATENT DOCUMENTS

| | | | |
|---|---|---|---|
| 5,948,429 A | * | 9/1999 | Bell et al. .................. 424/426 |
| 6,022,727 A | | 2/2000 | Worden et al. |
| 6,087,158 A | | 7/2000 | Worden et al. |
| 6,224,893 B1 | | 5/2001 | Langer et al. |
| 6,281,256 B1 | | 8/2001 | Harris et al. |
| 6,471,993 B1 | | 10/2002 | Shastri et al. |

OTHER PUBLICATIONS

Sebba, F., "An Improved Generator for Micron-Sized Bubbles," *Chemistry and Industry* 3:91-92, 1985.

* cited by examiner

*Primary Examiner*—Sandra E. Saucier
*Assistant Examiner*—Lora E Barnhart
(74) *Attorney, Agent, or Firm*—Christensen O'Connor Johnson Kindness PLLC (57) ABSTRACT

In one aspect the present invention provides biodegradable, porous structures that each include a structural framework, wherein the structural framework includes: (a) a solidified mixture of polymer molecules and amino acid molecules, wherein at least some of the amino acid molecules are linked to other amino acid molecules within the framework; and (b) a multiplicity of interconnected spaces defined by the structural framework. In some embodiments, the porous structures of the invention are adapted to physically support the growth of living cells in vitro or in vivo, and can be used to grow living tissue and/or living organs. The present invention also provide methods for making the biodegradable, porous structures of the invention.

22 Claims, 3 Drawing Sheets

POROUS STRUCTURES USEFUL FOR GROWING LIVING TISSUE, AND METHODS OF MANUFACTURE

CROSS-REFERENCE TO RELATED APPLICATION

This application claims the benefit of U.S. Provisional Application No. 60/339,129, filed Dec. 6, 2001.

STATEMENT REGARDING FEDERALLY SPONSORED RESEARCH OR DEVELOPMENT

This invention was made with government support under grant number EEC 9529161, awarded by the National Science Foundation. The government has certain rights to this invention.

FIELD OF THE INVENTION

This invention relates to scaffolds for growing living tissue and organs in vitro or in vivo.

BACKGROUND OF THE INVENTION

Trauma and disease can lead to the complete or partial loss of tissue, or a whole organ. Surgical strategies to deal with tissue loss include organ transplantation from one individual to another, tissue transfer from a healthy site to the affected site in the same individual, and replacement of tissue function with mechanical devices such as prosthetic joints and dialysis machines. Additional strategies include pharmacologic supplementation of the metabolic products of absent or nonfunctional tissue.

These strategies have a number of inherent limitations. For example, supplementation of metabolic products of diseased organs is currently most commonly used in endocrinology. Hormonal products, such as insulin, thyroid, adrenal, or gonadal hormones can be continuously supplemented. The lack of normal feedback mechanisms, though, may result in an imbalance of hormone levels, causing acute or long-term complications.

Non-biological materials are used routinely in ophthalmology (e.g., intraocular lenses), traumatology (e.g., replacement of joints), cardiovascular surgery (e.g., mechanical heart valves, vascular prostheses, and stents), and reconstructive and cosmetic surgery. These materials are also used for extracorporeal devices, such as dialysis or plasmapheresis apparatuses. Major complications include infection, lack of biocompatibility and limited material durability.

Surgical reconstruction, such as using different organs, or unaffected tissue, to replace diseased tissue or organ, also has its limitations. The replacement organs may include different tissue types, may not be able to properly function in the new environment, and may be unable to completely replace lost function. Morbidity at the donor site is a major concern.

Organ transplantation of kidney, liver, heart, lung, and pancreas has made many innovative advances in recent years. Unfortunately, however, organ transplantation is severely limited by an increasing donor shortage. The other major problems are the high cost of the procedures, and the necessity of lifelong immunosuppression with its serious side effects.

On the other hand, the technique of tissue engineering seeks to replace or restore damaged or defective tissue and organs with constructs that include specific populations of living cells that meet the needs of the damaged portion of the recipient. A problem in the field of tissue engineering, however, is the provision of support structures, often called scaffolds, that physically support and promote the growth of different cell types, in vitro or in vivo, to form new tissue or organs. Preferably the scaffolds are resorbed by the cells which grow around and within them. Accordingly, the present invention provides structures useful, for example, for physically supporting growing tissue and organs in vitro and in vivo, and methods of making the structures.

SUMMARY OF THE INVENTION

In one aspect the present invention provides biodegradable, porous structures that each include a structural framework, wherein the structural framework includes: (a) a solidified mixture of polymer molecules and amino acid molecules, wherein at least some of the amino acid molecules within the framework are linked to other amino acid molecules within the framework; and (b) a multiplicity of interconnected spaces defined by the structural framework. In some embodiments, the porous structures of the invention are adapted to physically support the growth of living cells in vitro or in vivo, and can be used to grow living tissue and/or living organs.

In another aspect, the present invention provides methods for making biodegradable, porous structures that each include a multiplicity of interconnected spaces defined by a structural framework. The methods of this aspect of the invention each include the steps of: (a) making an aphron from a population of molecules, wherein said population comprises molecules selected from the group consisting of (1) biodegradable polymer molecules, and (2) a mixture of amino acid molecules and polymer molecules; (b) freezing the aphron in a mold to yield a frozen, porous, structure comprising a multiplicity of interconnected spaces defined by a structural framework; and (c) lyophilizing the frozen, porous, structure to yield a biodegradable, porous structure comprising a multiplicity of interconnected spaces defined by a structural framework. The methods of this aspect of the invention can be used, for example, to make the biodegradable, porous structures of the present invention.

In another aspect, the present invention provides methods for growing a living tissue and/or a living organ. The methods of this aspect of the invention each include the steps of (a) introducing living cells into a biodegradable, porous structure that comprises a structural framework, wherein the structural framework comprises: (1) a solidified mixture of polymer molecules and amino acid molecules, wherein at least some amino acid molecules within the structural framework are linked to other amino acid molecules within the structural framework; and (2) a multiplicity of interconnected spaces defined by the structural framework; and (b) culturing the cells within the porous structure under conditions that promote formation of a living tissue or a living organ. The methods of this aspect of the invention can be practiced in vitro or in vivo. The porous structures of the present invention can be used in the methods of this aspect of the invention to grow a living tissue and/or a living organ.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

In one aspect, the present invention provides biodegradable porous structures comprising a structural framework, wherein the framework comprises: (a) a solidified mixture of polymer molecules and amino acid molecules, wherein at least some amino acid molecules within the framework are linked to other amino acid molecules within the framework; and (b) a multiplicity of interconnected spaces defined by the structural framework.

The porous structures of the invention are useful in any situation in which a porous structure is required. The porous structures of the invention are useful, for example, as frameworks on which, and within which, living cells can grow to form living tissue or a living organ. The living cells can grow within the interconnected spaces defined by the structural framework to form a tissue, or organ, having a shape that is at least partially determined by the shape of the porous structure. For example, the porous structures can be used as scaffolds to direct the three dimensional growth of allogenic or autologous cells, such as cardiomyocytes, chondrocytes, and hepatocytes, to regenerate specific tissues or organs, by in vitro or in vivo methods, for the development of tissues and organs to replace diseased, defective, or injured tissues or organs.

Again by way of example, the porous structures can be used for guided tissue regeneration in bone and dentistry. The porous structures can be used to prevent epithelial cell downgrowth into defect sites in bone tissue anywhere in the body, or into periodontal bony structure defects. By controlling epithelial cell downgrowth, other cells, such as periodontal ligament cells or bone tissue generating cells in the defect site, have a chance to regenerate the bony matrix.

Again by way of example, adipose surrogates are needed to sculpt contour deformities, such as the deformities caused by resection of tumors in the head, neck, and other trauma, and in the case of congenital abnormalities. Mature adipose tissue does not transplant effectively, and numerous natural, synthetic, and hybrid materials have been used instead. The porous structures of the invention can be used to grow adipose tissue in a desired shape, which can be used to sculpt contour deformities.

The porous structures of the invention can also be applied to the site of bleeding during surgery to slow or stop the bleeding. The porous structures can also include one or more factors that promote blood clotting. The porous structures can also be used, for example, as embolic agents to block blood supply to a deep seated brain tumor that may be difficult to remove by conventional surgical techniques.

Other uses for the porous structures of the invention include use as support structures for gas and solution phase catalysis, support structures for solid phase synthesis, immobilized beds in reactors and thermal insulations, filters, matrix materials for preparation of porous ceramic materials, medical scrubs, swabs, and sponges.

The porous structures of the invention are biodegradable so that they are ultimately broken down by the cells that grow within and around them. Polymer molecules incorporated within the structural framework may or may not be biodegradable. When biodegradable polymer molecules are not incorporated within the structural framework, the cross-linked amino acid molecules confer the property of biodegradability on the porous structure. The amino acids are degraded by the cells that grow within and around the porous structure, thereby causing the physical degradation of the structural framework.

Polymers that are useful as components of the structural framework can be dissolved in a solvent and the resulting solution used to make the structural framework. Representative examples of biodegradable polymers that are useful as components of the structural framework include: collagen and its derivatives; proteins; polysaccharides, such as alginate, dextran, gellans, starch, cellulose, hyaluronic acid and its synthetic derivatives; fibrin; chitosan; and synthetic polymers, such as some poly(hydroxy acids) such as poly(lactic acid)(PLA), poly(glycolic acid)(PGA), poly(lactic acid-glycolic acid copolymers)(PLGA), polyglycolides, aliphatic polyesters, poly(esteramides), polyamides, polyanhydrides, polyorthoesters, some polyurethanes, and polyphosphazenes.

Representative examples of polymers that are not biodegradable, and that are useful as components of the structural framework include: polyethylene glycol, polyethylenoxide, polyvinyl alcohol, polyethylene oxide-polypropylene oxide copolymer, polyvinyl pyrrolidone, polyhydroxy ethyl methacrylate, polysiloxanes, polycarbonates, and polyacrylates. U.S. Pat. No. 6,471,993, which is incorporated herein by reference, discloses numerous other, representative, examples of polymers that are useful as components of the structural framework.

A mixture of different polymers can be included in the structural framework to yield a structural framework that possesses one or more desired physical, chemical and/or biological properties. Thus, for example, polymer blends, grafts, copolymers, interpenetrating polymer networks and semi-interpenetrating polymer networks are all useful as components of the structural framework. Such polymer mixtures may, for example, enhance physical properties, such as mechanical strength, or thermal properties, and/or enhance biological function or rate of biodegradability of the structure. The polymers in the mixture are typically miscible in a common solvent, or in a combination of solvents, to facilitate manufacture of the structure.

The structural framework includes amino acid molecules, wherein at least some of the amino acid molecules within the structural framework are linked to other amino acid molecules within the structural framework. All amino acid molecules, including natural and synthetic amino acid molecules, and mixtures of amino acid molecules, are useful as components of the structural framework. Representative examples of useful amino acids include: aspartic acid, isoleucine, threonine, leucine, serine, tyrosine, glutamic acid, phenylalanine, proline, histidine, glycine, lysine, alanine, arginine, cysteine, tryptophan, valine, glutamine, methionine, and asparagine.

The presence of linkages between amino acids provides structural stability to the structural framework. The amino acid molecules incorporated within the structural framework are chosen so that they possess functional groups that are capable of forming linkages with other amino acids within the structural framework. The linkages can be non-covalent linkages and/or covalent linkages. Examples of non-covalent linkages include hydrogen bonds, electrostatic interactions, hydrophobic interactions, Van der Waals interactions, and salt bridges. For example, cationic and anionic groups present on amino acids within the structural framework can interact electrostatically.

Covalent linkages can be formed between any suitable chemical groups present in amino acid molecules within the biodegradable structures of the invention. For example, amino acids that are easily derivatizable at their side chains include aspartic acid, glutamic acid, lysine, arginine, cysteine, histidine, tyrosine, methionine and tryptophan. These nine amino acids contain the following eight principal functional groups that can be covalently linked: primary amines ($NH_2$), carboxylate (COOH), sulfhydryls or disulfides (SH or S—S), thioethers (found in methionine), imidazolyls (found in histidine), guanidinyl groups (found in arginine), phenolic (found in tyrosine), and indolyl (found in tryptophan). These functional groups can be covalently linked using any suitable chemical reaction, such as the methods disclosed in *Bioconjugate Techniques*, Greg T. Hermanson, Academic Press (1996), which publication is incorporated herein by reference.

Any reactive functional group present on polymer molecules within the structural framework can also be used to covalently, or non covalently, attach the amino acid molecules to the structural framework. Examples of non-covalent linkages include hydrogen bonds, electrostatic interactions, hydrophobic interactions, Van der Waals interactions, and salt bridges. Examples of chemical reactions useful for forming covalent linkages between functional groups on polymer molecules and functional groups on amino acids are set forth in *Bioconjugate Techniques*, Greg T. Hermanson, Academic Press (1996), or using chemical reactions available in the art and described, for example, in March, "Advanced Organic Chemistry", $4^{th}$ Edition, 1992, Wiley-Interscience Publication, New York, which publication is incorporated by reference herein.

The structural framework includes a solidified mixture of polymer molecules and amino acid molecules. In this context, the term "solidified" encompasses completely rigid structures, and also structures that are not completely rigid, but are sufficiently rigid to function as frameworks upon which, and within which, living cells can grow to form a tissue or organ. For example, the structural framework of some porous structures of the invention includes an alginate polymer that forms a firm gel which is not completely rigid.

Typically, the amount of polymer(s) varies with the amount of amino acid(s) in the structural framework. Representative parts by weight ratios of polymer(s) to amino acid(s) in the structural framework are from 25:75 to 100:1.

The structural framework defines a multiplicity of interconnected spaces within which living cells can grow and divide to form a tissue or organ. In some embodiments, the average diameter of the spaces (measured at the widest point of the space) is between 1 μm and 300 μm, such as from between 1 μm and 100 μm.

In some embodiments, the porous structures of the invention include one or more types of biologically active molecules incorporated within, and/or on, the structural framework. The biologically active molecules can confer one or more desirable properties on the structures of the invention. For example, the biologically active molecules can enhance growth of cells, promote cell migration, promote cell division, promote cell proliferation and differentiation, stimulate formation of different phenotypic modifications of cells, promote angiogenesis, promote vascularization, and promote extracellular matrix deposition.

Examples of biologically active molecules that can be attached to the structural framework include: growth factors, such as TGF-α and TGF-β; fibronectin; laminin; vitronectin; integrins; nucleic acid molecules; lipids; and sugars. Also, nucleic acid molecules (e.g., genes, plasmid DNA, naked DNA, and antisense molecules) can be attached to the structural framework.

Typically, the biologically active molecules are attached, covalently or non-covalently, to the amino acids or to the polymer(s) incorporated within the structural framework. Examples of functional groups, present on amino acids, useful for covalently attaching biologically active molecules to the amino acids present within the structural framework include: primary amines ($NH_2$), carboxylate (COOH), sulfhydryls or disulfides (SH or S—S), thioethers, imidazolyls, guanidinyl groups, phenolic, and indolyl. Any reactive functional group present on polymer molecules within the structural framework can be used to covalently attach biologically active molecules to the structural framework.

The following publications describe examples of technologies that are useful for attaching biologically active molecules to polymers, such as the polymers present in the structures of the present invention: Nuttelman, C. R., et al., *Journal of Biological Materials Research* 57:217–223 (2001); Rowley, J. A., et al., *Biomaterials* 20:45–53 (1999); Hubbel, J. A., *Biomaterials for tissue Engineering Biotechnology* 13:565–76 (1995); Massia, S. P., and Hubbell, J. A., *Anal. Biochem* 187:292–301 (1990); Drumheller, P. D., et al., *Anal. Biochem.* 222:380–388 (1994); Kobayashi, H., and Ikada, Y., *Current Eye Res.* 10: 899–908 (1991); Lin, H. B., et al., *J. Biomaterial Sci. Polym. Ed.* 3:217–227 (1992); and Bellamkonda R., et al., *J. Biomed. Material Research* 29:663–71 (1995).

The biologically active molecules can be attached to every part of the structural framework, or to only a portion of the structural framework. For example, in some embodiments, that are adapted to be implanted into a living animal, biologically active molecules that act to decrease the foreign body reaction (e.g., antiinflammatory agents, and immunomodulatory agents) are attached only to the surface(s) of the structure that is/are in contact with living tissue in the animal body. The biologically active molecules serve to decrease the foreign body reaction of the living body against the implanted structure.

Figure 1:
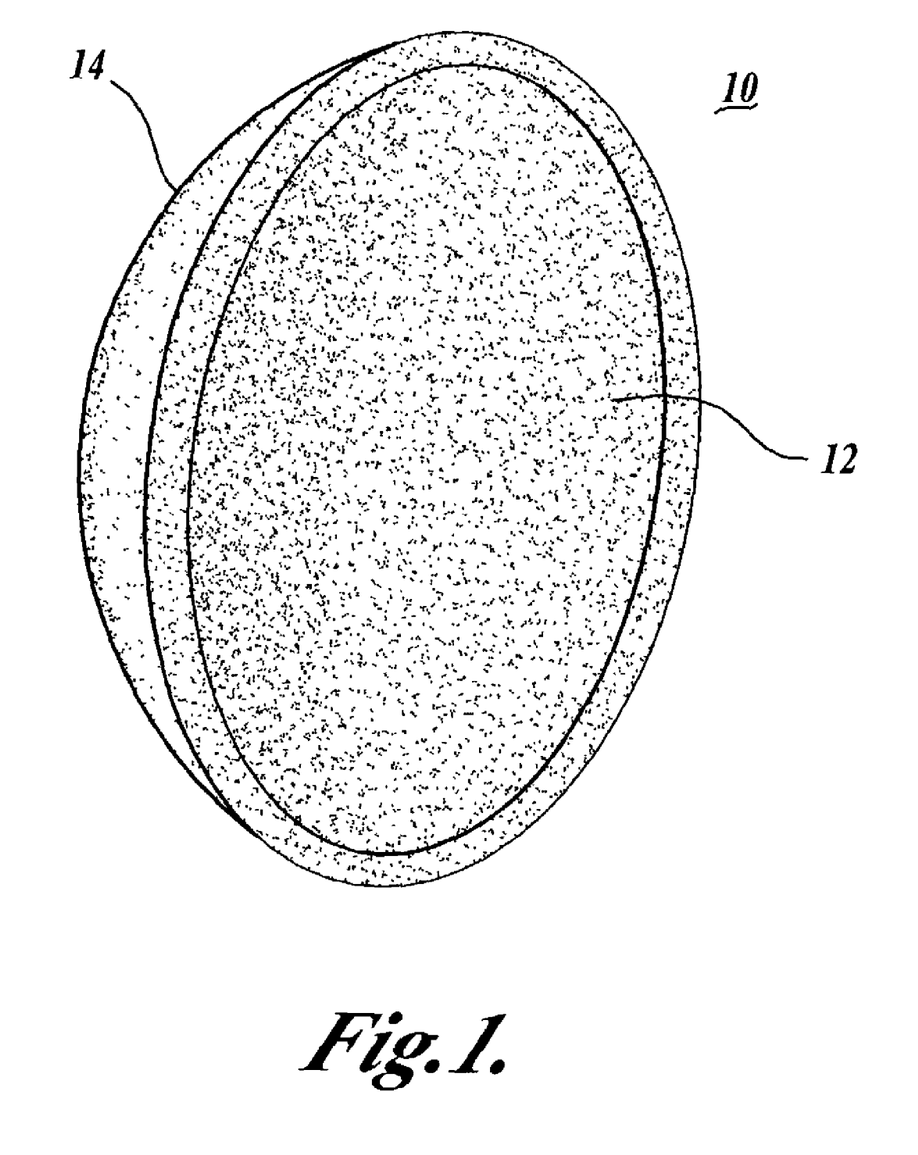
FIG. 1 shows a representative example of a biodegradable, porous structure of the invention.
Figure 2:
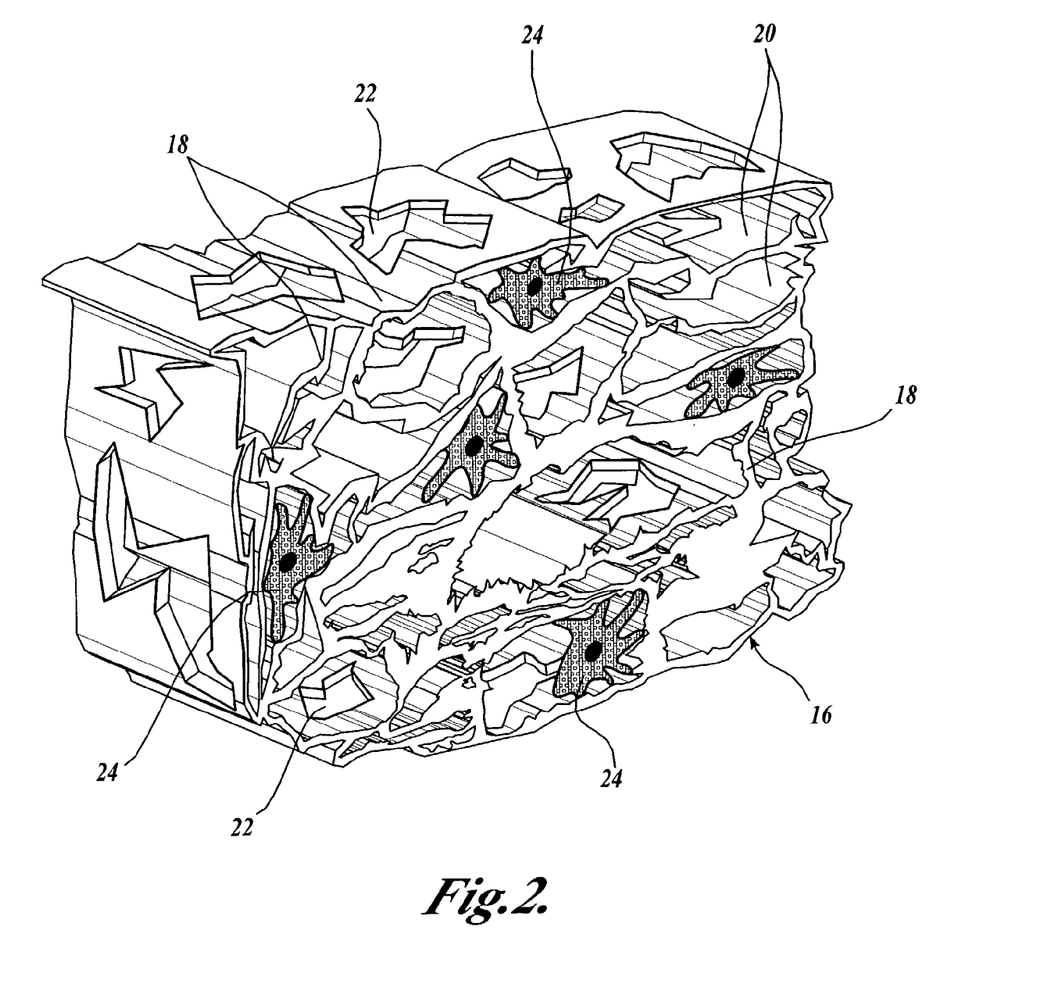
FIG. 2 shows a portion of a biodegradable, porous structure of the invention, wherein a structural framework defines a multiplicity of interconnected spaces. Cells are shown in some of the spaces.
Figure 3:
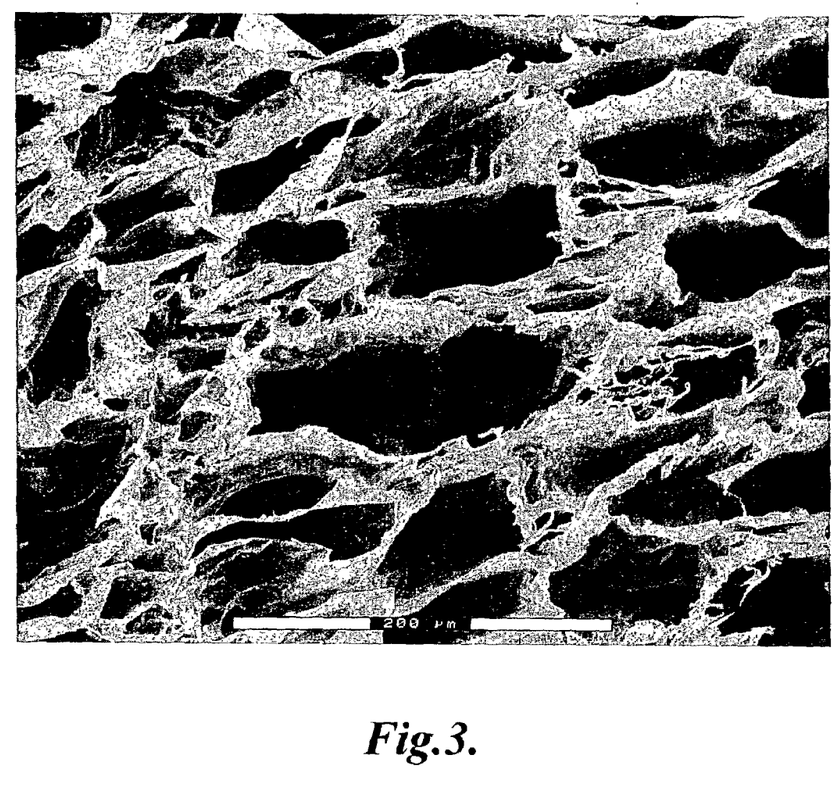
FIG. 3 shows an electron microscopic image of a portion of a biodegradable, porous structure of the invention that is described in Example 1.

The shape and dimensions of a tissue, or organ, grown on a porous structure of the invention is completely, or partially, determined by the shape and dimensions of the structural framework. Thus, the shape and dimensions of the structural framework can be selected to yield a tissue or organ having a desired shape and dimensions. For example, FIG. 1 shows a representative example of a biodegradable porous structure of the invention. Structure 10 includes an inner surface 12 and an outer surface 14. As shown more clearly in the drawing of a magnified portion of structure 10 shown in FIG. 2, structure 10 includes a three-dimensional structural framework 16 comprising numerous interconnected framework elements 18. Structural framework 16 defines a multiplicity of spaces 20 that are connected by a multiplicity of pores 22 that penetrate framework elements 18. Living cells 24 can penetrate structure 10 and grow within spaces 20. By way of further illustration, FIG. 3 shows an electron microscopic image of a portion of a representative structure 10 of the invention. Structural framework 16 and spaces 20 are visible. It will be understood by those of skill in the art that the shape and dimensions of framework elements 18, spaces 20 and pores 22 depend on a variety of factors, such as the materials and manufacturing conditions used to make structure 10.

Structure 10 shown in FIG. 1 can, for example, be seeded with chondrocytes which grow throughout structure 10 to yield a cartilaginous structure having a shape that is identical, or substantially similar, to the shape of structure 10. Thus, the cartilaginous structure can, for example, be applied to a complementary surface within a living body, such as the curved surface of the distal end of a human femur which forms an articulating surface within the knee, and is normally covered with a protective layer of cartilage. The cartilaginous structure can therefore be used to replace damaged cartilage on the end of the femur within a human knee.

The porous structures of the invention can be made, for example, using the methods of the invention for making a biodegradable, porous structure, as described herein.

In another aspect, the present invention provides methods of making a biodegradable, porous structure comprising a multiplicity of interconnected spaces defined by a structural framework. The methods of this aspect of the invention each comprise the steps of: (a) making an aphron from a population of molecules, wherein said population comprises molecules selected from the group consisting of (1) biodegradable polymer molecules, and (2) a mixture of amino acid molecules and polymer molecules; (b) freezing the aphron in a mold to yield a frozen, porous, structure comprising a multiplicity of interconnected spaces defined by a structural framework; and (c) lyophilizing the frozen, porous, structure to yield a lyophilized, biodegradable, porous structure comprising a multiplicity of interconnected spaces defined by a structural framework. Optionally, the methods of this aspect of the invention comprise the further step of covalently linking at least some of the amino acid molecules in the lyophilized structure.

Some methods of this aspect of the invention each comprise the steps of: (a) making an aphron from a population of molecules, wherein said population comprises a mixture of amino acid molecules and polymer molecules; (b) freezing the aphron in a mold to yield a frozen, porous, structure that comprises a structural framework, wherein the framework comprises: (1) a solidified mixture of polymer molecules and amino acid molecules, wherein at least some of the amino acid molecules are linked to other amino acid molecules; and (2) a multiplicity of interconnected spaces defined by the structural framework; and (c) lyophilizing the frozen, porous, structure to yield a lyophilized, biodegradable, porous structure comprising a multiplicity of interconnected spaces defined by a structural framework.

The term "aphron" refers to a phase (e.g., a gas phase, liquid phase, or solid phase) encapsulated by an aqueous soapy shell. As used herein, the term "aphron" encompasses, for example, a multiplicity of connected bubbles, each bubble bounded by an encapsulating soapy film. Aphrons are described in F. Sebba, "Foams and Biliquid Foams-Aphrons", John Wiley & Sons, 1987, which publication is incorporated herein by reference.

An example of a device for making aphrons useful in the practice of the methods of the present invention is described by Sebba, F., *Chemistry & Industry* No.3, pp. 91–92 (1985), which publication is incorporated herein by reference. This device is also disclosed in FIG. 5.1 of the Sebba textbook "Foams and Biliquid Foams-Aphrons", John Wiley & Sons, 1987. Another example of a device for making aphrons useful in the practice of the present invention is described in U.S. Pat. No. 6,087,158 (see, e.g., FIG. 3 therein), which patent is incorporated herein by reference in its entirety.

In some embodiments, the aphron is made from biodegradable polymer molecules, such as the biodegradable polymer molecules described herein in connection with the porous structures of the invention. In other embodiments, the aphron is made from polymer molecules that are not biodegradable, such as the non-biodegradable polymer molecules described herein in connection with the porous structures of the invention. In other embodiments, the aphron is made from a mixture of polymer molecules that are not biodegradable, and polymer molecules that are biodegradable. In the embodiments of the methods of the invention that do not use biodegradable polymer molecules, the aphron is made from a mixture of polymer molecules that are not biodegradable, and amino acid molecules, and at least some of the amino acid molecules are linked (covalently or non-covalently) to each other in the lyophilized structure. The linked amino acids impart structural stability to the porous structures. The amino acid molecules are biodegradable and are degraded by the tissue, or organ, that forms around the structure, thereby causing the porous structures to degrade over time as the cells grow in and around the porous structures.

Useful polymers and amino acids can be dissolved in a solvent and the resulting solution used in the methods of this aspect of the invention to make a porous, biodegradable, structure. Polymers and amino acids can be dissolved in the same solvent, or can be dissolved in different solvents, provided that the resulting solutions can be mixed and used in the methods of the invention. The choice of solvent depends on the chemical nature of the polymer(s) and/or amino acid(s) that are to be dissolved. For example, some polymers are soluble in halogenated solvents, such as methylene chloride, chloroform, carbon tetrachloride, dichloroethane, trichloroethylene, and hexafluoroisopropanol. Water-soluble polymers can be dissolved in water or relatively polar organic solvents such as alcohols, ethyl acetate, acetone, dimethylsulfoxide, dimethylformamide, ethers, glymes, phenols, and chloroform. Those of skill in the art can readily determine an appropriate solvent for dissolving a polymer.

By way of specific example, polymers such as alginates and poly vinyl alcohol (PVA), and almost all amino acids, dissolve in water and aqueous buffers. PVA also dissolves in water-ethanol mixtures. Again by way of example, polyurethanes dissolve in dimethylacetamide and dimethyl formamide. These two solvents also dissolve hydrophilic or polar amino acids. Ethanol is a useful solvent for dissolving many polymers and amino acids. Other representative examples of useful solvents include acetone, ethylacetate, methylene chloride, chloroform, hexafluoroisopropanol, and chlorinated aromatic hydrocarbons. Examples of solvents useful for dissolving specific polymers are set forth in the first two columns of Table 1 of U.S. Pat. No. 6,471,993, which patent is incorporated herein by reference.

The aphron is frozen in a mold to yield a frozen, porous, structure. The aphron may be frozen to any temperature below its freezing point, such as freezing to approximately −20° C., or lower, in liquid nitrogen, or in any suitable freezing medium, or in a freezing apparatus. Freezing the aphron preserves the structure of the aphron. The shape of the mold is chosen to yield a porous structure having a desired shape and dimensions. The frozen, porous, structure is then lyophilized thereby preserving the shape and porosity of the structure.

In the embodiments of the methods of the invention that do not use biodegradable polymer molecules to form the aphron, the aphron is made from a mixture of polymer molecules that are not biodegradable, and amino acid molecules. At least some of the amino acid molecules are linked (covalently and/or non-covalently) in the lyophilized structure. All amino acid molecules are useful in these embodiments of the methods of the invention. Representative examples of useful amino acids are set forth herein in connection with the porous structures of the invention. The amino acid molecules are chosen so that they possess functional groups that are capable of forming linkages with other amino acids. In some embodiments, biologically active molecules are attached to the structural framework. For example, biologically active molecules can be mixed with the polymer molecules during preparation of the aphron, or can be covalently attached to the structural framework of the lyophilized structure. Representative examples of biologically active molecules are described herein in connection with the biodegradable, porous structures of the invention.

In another aspect, the present invention provides methods for growing a living tissue and/or a living organ. The methods of this aspect of the invention each include the steps of (a) introducing living cells into a biodegradable porous structure comprising a structural framework, wherein the structural framework comprises: (1) a solidified mixture of polymer molecules and amino acid molecules, wherein at least some amino acid molecules within the structural framework are linked to other amino acid molecules within the structural framework; and (2) a multiplicity of interconnected spaces defined by the structural framework; and (b) culturing the cells within the porous structure under conditions that promote formation of a living tissue or a living organ. The methods of this aspect of the invention can be practiced in vitro or in vivo. The porous structures of the present invention can be used in the methods of this aspect of the invention to grow a living tissue and/or a living organ. Exemplary living tissues that can be made using the methods of this aspect of the invention include skin, cartilage, blood vessels, muscle, tendon, and ligament. Exemplary living organs that can be made using the methods of this aspect of the invention include liver, pancreas and heart. The tissues and/or organs made using the methods of this aspect of the invention can be used, for example, to replace or repair damaged or diseased tissue or organs in a living body, such as a mammalian body, such as a human body.

The following examples merely illustrate the best mode now contemplated for practicing the invention, but should not be construed to limit the invention.

EXAMPLE 1

This Example describes the manufacture of representative porous structures of the invention. The porous structures described in this Example are useful as scaffolds for physically supporting the growth of living cells.

Materials and Methods: The amino acids glycine, lysine, and norleucine (also called isoleucine), were obtained from Sigma Chemical Company, U.S.A. Alginic acid, sodium lauryl sulfate (SDS), dicyclohexyl carbodiimide (DCC), dichloro methane, and calcium chloride ($CaCl_2$) were from Aldrich, U.S.A.

Aqueous alginic acid solutions at 2% (w/v) and 5% (w/v) were stirred with a mixture of amino acids and the surfactant SDS in specific proportions in a colloidal aphron generator (Sebba, F., *Chem and Ind.* 3:91 (1985)) to form a viscous aphron of polymer-amino acid. The proportions of alginate, glycine, lysine and leucine in the 2% alginic acid solution were 33.94, 59.39, 5.94 and 0.73, respectively. The proportions of alginate, glycine, lysine and leucine in the 5% alginic acid solution were 32.81, 56.24, 7.63 and 3.32, respectively. The amount of sodium dodecyl sulfate (SDS) was 1.25% (w/v), and was the same in the 2% and 5% alginate solutions. The proportion of each ingredient in the solution used to make the aphrons was calculated using the relationship: actual weight of constituent/total weight of all constituents X 100.

The aphron was poured into molds and frozen at −80 C., and then lyophilized. The lyophilized aphron was first allowed to gel by dropping into a 4% $CaCl_2$ solution. Gelation took place immediately and the gels were then dried with acetone at room temperature. The amino acids were further crosslinked by biconjugate peptide synthetic methods using excess DCC in dichloromethane for 16 hours. The scaffolds were then washed with dichloromethane and water to remove any isourea byproducts, and subsequently lyophilized.

A Perkin Elmer 1720 FTIR was used to record the spectra of the materials and to investigate the crosslinking of the amino acids.

Scanning electron microscope (ESEM) images were obtained using an environmental SEM with a gun voltage set at 15 torr, and a chamber pressure of 5 torr. The volume of interconnected pores within scaffolds was determined by measuring the total volume of the scaffold and the amount of solvent required to fill the porous component. In brief, the scaffolds, in the form of discs, were placed in a graduated cylinder filled with a known volume of ethanol ($V_1$). The total volume following the scaffold immersion was recorded ($V_2$). The scaffolds were removed with the entrapped solvent in the pores, and the remaining volume of ethanol in the graduated cylinder was denoted as ($V_3$). The total volume of the scaffold ($V_T$) was calculated according to Equation (1), and the porosity, P, was determined using Equation (2)

$$V_T = V_2 - V_3 \tag{1}$$

$$P = (V_1 - V_3)/V_T \tag{2}$$

Disc shaped scaffolds of 12 mm diameter and 3 mm thickness were hydrated with phosphate buffered saline and the compression properties of the wet disc were evaluated using a custom built compression tester. The compression Stress ($\zeta$) and Strain percentage ($\sigma$) were calculated using Equations (3) and (4) respectively.

$$\zeta = F/A \tag{3}$$

where F=Force and A=area of the sample $$\sigma = 1/h \times 100 \tag{4}$$

where l is change in displacement, and h is the initial thickness of the sample.

The initial modulus was determined from the initial slope of the stress strain curve.

Porous scaffold discs of 6 mm diameter were sterilized by ethylene oxide and allowed to deaerate before subcutaneous implantation in the dorsal area of mice. Anaesthetized, wild type, three month old mice were used for the study. The implants were retrieved after a period of four weeks, fixed in 10% formalin for 24 hours, and processed for embedding in paraffin and sectioning as per standard procedures. Massons trichrome stain was used to stain sections for the histological study.

Results: In the present example, supersaturated amino acids were mixed with a biodegradable natural polymer, alginic acid, to form a colloidal aphron using the method of Sebba (*Chem and Ind.* 3:91 (1985)). The viscous solid foam produced was immediately frozen to hold the structure and lyophilized using controlled conditions to preserve the structure. The scaffold formed was first dropped into a calcium chloride solution to gel by ionically crosslinking the carboxylic groups of the polymer backbone, with chelating $Ca^{2+}$ ions. Gelation was instantaneous and homogenous on account of the high pore volume and porous structure of the scaffold, and the high ionic strength of the cations. The DCC crosslinking reactions were performed in organic solvent dichloromethane and in anhydrous conditions for increased efficiency.

The alginate infrared (IR) spectrum showed characteristic peaks at 3383 $cm^{-1}$ (OH str), 1607 $cm^{-1}$ (OOOH str) and 1036 $cm^{-1}$ (C—O—C str). A typical alginate-amino acid IR spectrum revealed bands at 3467 $cm^{-1}$ and 2200 $cm^{-1}$ which indicate the presence of NH groups in the structure. Amide crosslinks are observed by the shifting of the carboxylic peak to 1620 $cm^{-1}$.

A typical ESEM micrograph of the alginate amino acid scaffold is shown in FIG. 3, and clearly shows the three-dimensional, structural framework and interconnected spaces. The diameters of the interconnected spaces are in the range of 10 μm to 50 μm, which is a suitable size for promotion of neovascularization and reduction of foreign body capsule as per the studies of Brauker et al. (*Journal of Biomedical Materials Research* 29:1517–1524 (1995)). The total volume of the interconnected spaces ranged from 65 to 85% depending on the amount of alginate in the scaffold.

The compressive Stress vs. Strain curve of the materials showed that the materials are inelastic. The Compression Stress (ζ) and initial modulus values of the scaffolds from Eqn 3, and Stress vs. Strain curve, change from 12.09±1.05 KPa and 5.95±2.60 KPa to 9.08±0.78 KPa and 16.19±7.37 KPa, respectively, when the alginate solution concentration used in the preparation of the scaffold was varied from 2% (w/v) to 5% (w/v). The mechanical properties of the scaffold are suitable for use in tissue engineering applications of soft tissue.

The implantation data demonstrated the utility of the structures to allow cell invasion and vascularization. Alginate is currently used for several applications including wound healing. Depending on its purity and chemical structure, alginate can elicit a mild inflammatory response (see, e.g., Odel, E. W., et al., *Br. J. Oral. Maxillo. Surg.* 32(3): 178–179 (1994)). The addition of RGD-containing peptides has been shown to permit endothelial, preadipocyte, and fibroblast cell adhesion and proliferation on the material (see, e.g., Rowley, J. A., et al., *Biomaterials* 20:45–53 (1999)). A histological section showed a thin fibrous capsule indicative of very minimal foreign body reaction and negligible inflammatory response. The section also showed the presence of collagen and integration of the scaffold and tissues with the underlying muscle structure, which is important for tissue engineering applications. Some blood vessels were also present, indicating that the interconnected spaces were large enough to allow for vascularization of the scaffold.

EXAMPLE 2

This example describes the use of a porous structure of the invention to make a heart valve.

Porous structures were fabricated by the technique of colloidal aphron formation. A blend of the hydrogel, polyvinyl alcohol (Molecular weight 195,000), and the amino acids glycine and lysine, were used to formulate the structures using an aphron generator (Sebba, F., *Chem. & Ind.* 91:25–26 (1985)). The aphrons were frozen, lyophilized, and cross linked using carbodiimide, to obtain structures with adequate mechanical properties for handling and for tissue growth.

The structures were cleaned and sterilized using ethylene oxide gas, and then seeded with bovine valve endothelial cells (BVEC), Passage 9 (in Waymouth's medium with 5% Fetal bovine serum (FBS)), Bovine valve interstitial cells (BVIC), Passage 13 (in Dulbecco's Modified eagle's medium with 10% FBS) and Bovine aortic endothelial cells (BAEC), Passage 14 (in Waymouth's medium with 5% FBS). Non-seeded controls either in Waymouth's with 5% FBS, or Dulbeccos Modified Eagle's Medium (DMEM) with 10% FBS were used for the Alamar Blue assay. The structures were wedged in 48 well plates, to prevent floating, during overnight seeding with 100,000 cells in 500 μl of medium.

On day 2, all the constructs were transferred to 12 well plates with 2 ml media for further growth. On day 3, half of the constructs were fixed with 10% formalin and labeled with 2 μM calcein AM and 4 μM ethidium homodimer-1 for fluorescent labeling, to image the live/dead cells. Images were taken on a Nikon E800 microscope, with a 10× objective, with FITC and Rhodamine fluorescence filters. The Alamar blue assay was also done to assess viability of cells in the structures. For this assay, on Day 4 the structures were incubated in 10% Alamar Blue solution in culture media (800 μL media with 80 μL Alamar Blue) for 4 hours at 37° C. 300 μL solution removed from the wells was placed into 96 well plates for spectrophotometric reading at 570 nm and 600 nm. The percentage reduction of substrate in the Alamar Blue assay (corrected for absorbance due to the medium alone) is proportional to the number of live cells present.

In the present study, the pore sizes of the structures ranged from 10 to 60 μm with a void volume of greater than 60%. No additional growth factors or cell adhesion promoting or proliferating molecules were used.

Bovine aortic endothelial cells adhered to the structures, and the cells remained viable for at least ten days. The cells were also observed to be present within the spaces of the porous architecture. Alamar Blue staining revealed living cells on the structures.

EXAMPLE 3

This Example describes the use of a representative porous structure of the invention to grow chondrocytes. The porous structure was prepared from the polymer alginate, and a mixture of the amino acids glycine, lysine and isoleucine.

Aphrons were made, as described in Example 1, from the polymer alginate, and a mixture of the amino acids glycine, lysine and isoleucine in the following ratio: 33.94: 59.39: 5.94: 0.73, respectively. The control was a 2% solution of sodium alginate (Sigma) prepared as a gel by the addition of 100 mM $CaCl_2$ and 150 mM NaCl.

$2.36 \times 10^6$ primary bovine articular chondrocyte cells were used to seed each porous structure. These cells were suspended in 300 μl of medium A. Medium A is Dulbecco's Modified Eagle's Medium (DMEM), plus 10% fetal bovine serum (FBS), non-essential amino acids (0.1 mM), gentamicin (25 μg/ml), 40 μg/ml L-proline and 50 μg/ml ascorbic acid.

Twenty four well plates of non tissue culture coated polystyrene were coated with agarose by polymerizing 200 μl of 2% agarose on each well plate prior to the start of experiment. Cells were suspended in Medium A, counted on a hemocytometer to determine cell number and assessment of viability. The cells were placed in the prepared wells under sterile conditions. Each portion of the porous structure was immersed in the cell culture until the entire scaffold was wet. After being immersed in cells, the porous structure was incubated for one hour then 2 ml culture medium were added. Thereafter, the medium was replaced every other day. The porous structures were moved to new plates every seven days.

The seeded structures were analyzed histologically after one day, 7 days, 15 days and 28 days. Structures were prepared for histology in 6-well plates and covered with 5 ml 100 mM barium chloride (BaCl) for 30 minutes to permanently crosslink the alginate so that the structures did not fall apart during processing. The structures were rinsed twice in phosphate buffered saline (PBS), in the presence of calcium and magnesium ions, for five minutes, and then placed in 10% neutral buffered formalin (NBF) at 4° C. After incubation in NBF for 48 hours, the structures were rinsed with 70% ethanol and stored in 70% ethanol, at 4° C., until embedding and sectioning.

At Day 1, cells were well distributed in the control alginate gels, and in the alginate-GLY-LYS-ISO porous structures of the invention. At Day 7, a comparative assessment of the control alginate gels, and the alginate-GLY-LYS-ISO porous structures of the invention, showed that the alginate-GLY-LYS-ISO porous structures had more healthy-looking cells with slightly more collagenous matrix deposition than the control alginate gels where many of the cells looked less healthy and pyknotic. Chondrocytes on the alginate-GLY-LYS-ISO porous structures at Day 7 showed fewer cells than in the alginate gel, however the cells were well dispersed throughout the matrix.

At Day 28, the histological sections of the control alginate gels showed chondrocyte cells that were healthy and expressing the cartilage phenotype. The cells had laid down a collagenous matrix similar to the matrix observed in normal cartilage, as evident by a darker purple staining, but outer portions of gel also had heavy infection with yeast and bacteria. A Masons trichrome stained section of this material revealed that the matrix was collagenous and a Saffranin-O stained section showed that a large portion of this collagen was of sulfated glycosoaminoglycans type indicating that true articular cartilage material was being laid down by the chondrocytes that had been seeded in these gels.

The histological sections of the alginate-GLY-LYS-ISO porous structures at the 28 day time point showed chondrocyte cells that were healthy and expressing the cartilage phenotype. The cells had laid down a collagenous matrix similar to the matrix observed in normal cartilage, as evident by a darker purple staining. Unlike the alginate gel controls, the alginate-GLY-LYS-ISO porous structures were not heavily infected. A Masons trichrome stained section of an alginate-GLY-LYS-ISO porous structure revealed that the matrix was collagenous, staining blue due to the chondrocytes embedded in the structure, and showing the natural phenotype of such cells. A Saffranin-O stained section showed that a large portion of this matrix was smooth and composed of sulfated glycosoaminoglycans (S-GAGS), indicating that native articular cartilage material was being laid down by the chondrocytes that had been seeded in the alginate-GLY-LYS-ISO porous structures.

Thus, the alginate-GLY-LYS-ISO porous structures successfully supported the growth and development of chondrocytes in vitro. Further, the alginate-GLY-LYS-ISO porous structures were mechanically more robust than the control alginate gels which tended to break apart during the course of the study. The alginate-GLY-LYS-ISO porous structures also appeared to be less susceptible to microbial infection than the control alginate gels.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method of making a biodegradable porous structure comprising a multiplicity of interconnected spaces defined by a structural framework, said method comprising:
   (a) stirring an aqueous solution in a colloidal aphron generator to form an aphron comprising a viscous foam, said aqueous solution selected from the group consisting of a solution of biodegradable polymer molecules and a solution of a mixture of amino acids and polymer molecules;
   (b) placing said aphron into a mold;
   (c) freezing the molded aphron to form a porous structure;
   (d) lyophilizing the porous structure; and
   (e) causing the porous structure to gel, yielding a lyophilized, biodegradable, porous structure comprising a multiplicity of interconnected spaces defined by a structural framework.

2. The method of claim 1 further comprising the step of covalently linking at least some of the amino acid molecules present in the lyophilized structure to other amino acid molecules present in the lyophilized structure.

3. The method of claim 1 wherein the biodegradable, porous structure is adapted to physically support the growth of living cells.

4. The method of claim 1 wherein the polymer molecules are selected from the group consisting of collagen, proteins, polysaccharide, fibrin, chitosan, poly(lactic acid), poly(glycolic acid), poly(lactic acid-glycolic acid copolymers), polyglycolides, aliphatic polyesters, poly(esteramides), polyamides, polyanhydrides, polyorthoesters, polyurethanes, and polyphosphazenes.

5. The method of claim 1 wherein the amino acid molecules are selected from the group consisting of aspartic acid, isoleucine, threonine, leucine, seine, tyrosine, glutamic acid, phenylalanine, proline, histidine, glycine, lysine, alanine, arginine, cysteine, tryptophan, valine, glutamine, methionine, and asparagine.

6. The method of claim 1 wherein the average diameter of the interconnected spaces is from 1 μm to 300 μm.

7. The method of claim 1 wherein the average diameter of the interconnected spaces is from 1 μm to 100 μm.

8. The method of claim 1 wherein the ratio of polymer molecules to amino acid molecules within the lyophilized, porous, structure is at least 25:75.

9. The method of claim 1 wherein the ratio of polymer molecules to amino acid molecules within the lyophilized, porous, structure is from 25:75 to 100:1.

10. The method of claim 1 further comprising covalently or non-covalently attaching biologically active molecules to the biodegradable polymer molecules or to the amino acid molecules that comprise said aphron, wherein said biologically active molecules are selected from the group consisting of growth factors, fibronectin, laminin, vitronectin, integrins, nucleic acid molecules, lipids, sugars, antisense molecules, antiinflammatory agents, immunomodulatory agents, molecules that promote cell migration, molecules that promote cell division, molecules that promote cell proliferation and differentiation, molecules that stimulate phenotypic modification of cells, molecules that promote angiogenesis, molecules that promote vascularization and molecules that promote extracellular matrix disposition.

11. The method of claim 1 wherein the aphron is made from a population of molecules comprising a mixture of amino acid molecules and polymer molecules, frozen in a mold to yield a frozen, porous, structure and lyophilized, and further wherein at least some of the amino acid molecules are linked to other amino acid molecules.

12. The method of claim 1 wherein the average diameter of the interconnected spaces is from 10 μm to 50 μm.

13. A method of making a biodegadable porous structure comprising a multiplicity of interconnected spaces defined by a structural framework, said method comprising:
 (a) stiring an aqueous solution in a colloidal aphron generator to form an aphron comprising a viscous foam, said aqueous solution comprising alginate, glycine, lysine, isoluecine, and sodium docecyl sulfate;
 (b) placing said aphron into a mold;
 (c) freezing the molded aphron to form a porous structure;
 (d) lyophilizing the porous structure; and
 (e) causing the porous structure to gel.

14. The method of claim 13 further comprising drying the gelled porous structure.

15. The method of claim 14 further comprising crosslinking the amino acids in the porous structure.

16. The method of claim 15 further comprising lyophilizing the porous structure.

17. The method of claim 13, wherein the alginate in the aqueous solution is 2% alginic acid (w/v) or 5% alginic acid (w/v).

18. The method of claim 13, wherein the aqueous solution comprises 2% alginate (w/v) and alginate, glycine, lysine, and isoleucine are present in proportions of about 33.94: 59.39:5.94:0.73, respectively.

19. The method of claim 13, wherein the aqueous solution comprises 2% alginate (w/v) and alginate, glycine, lysine, and isoleucine are present in proportions of about 32.81: 56.24:7.63:3.32, respectively.

20. The method of claim 13 wherein the amount of sodium dodecyl sulfate is about 1.25% (weight/volume).

21. A method of making a porous structure comprising a multiplicity of interconnected spaces defined by a structural framework, said method comprising:
 (a) stirring an aqueous solution in a colloidal aphron generator to form an aphron, said aqueous solution comprising polyvinyl alcohol, glycine, and lysine;
 (b) placing said aphron in a mold;
 (c) freezing the molded aphron to form a porous structure;
 (d) lyophilizing the porous structure; and
 (e) cross-linking the lyophilized porous structure using dicyclohexyl carbodiimide.

22. The method of claim 11, further comprising lyophilizing the cross-linked porous structure containing the linked amino acids.

* * * * *

UNITED STATES PATENT AND TRADEMARK OFFICE
CERTIFICATE OF CORRECTION

PATENT NO.        : 7,105,580 B2
APPLICATION NO.   : 10/314453
DATED             : September 12, 2006
INVENTOR(S)       : P.D. Nair et al.

It is certified that error appears in the above-identified patent and that said Letters Patent is hereby corrected as shown below:

On The Title Page Item (73) Assignee after "(US)" insert --and Georgia Tech Research Corporation, Atlanta, GA (US)--

On The Title Page Item (57) Abstract "provide" should read --provides--

Col 15 line 23 "stiring" should read --stirring--

Signed and Sealed this

Twenty-third Day of October, 2007

JON W. DUDAS
*Director of the United States Patent and Trademark Office*